United States Patent [19]

King et al.

[11] Patent Number: 4,539,414
[45] Date of Patent: Sep. 3, 1985

[54] 1H-CYCLOPENTA[B]BENZOFURAN DERIVATIVE AND ITS ANALOG

[76] Inventors: Ming L. King, 44-2, 25 Lung, 24-Hsiang, Section 4, Roosevelt Rd.; Chin-Chih Chiang, 4th Floor, No. 9, 44-Hsiang, Yu-Cheng Street; Han-Chin Ling, 3rd Floor, No. 24, 5-Lung, 626-Hsiang, Ting-Chou Rd., all of Taipei, Taiwan; Masahito Ochiai, 312, Kyoto University Shokuinshukusha, Gokanosho, Uji; Eiichi Fujita, 5-52, Fukakusananmei-cho, Fushimi, both of Kyoto, Japan; Andrew T. McPhail, Durham, N.C.

[21] Appl. No.: 542,140

[22] Filed: Oct. 14, 1983

[30] Foreign Application Priority Data

Apr. 14, 1985 [JP] Japan .................... 58-66280

[51] Int. Cl.³ ............... C07D 307/93; C07C 103/737
[52] U.S. Cl. ........................... 549/458; 564/171
[58] Field of Search ................... 549/458; 564/171

[56]  References Cited

PUBLICATIONS

King et al., J. Chem. Soc., Chem. Commun., vol. 20, pp.1150–1151, Oct. 15, 1982.
King et al., *Journal of Medical Science*, vol. 1, No. 1, pp. 11–20 (1975).

*Primary Examiner*—Henry R. Jiles
*Assistant Examiner*—Bernard I. Dentz
*Attorney, Agent, or Firm*—Pahl, Lorusso & Loud

[57]  ABSTRACT

Substantially pure compounds having the general formula

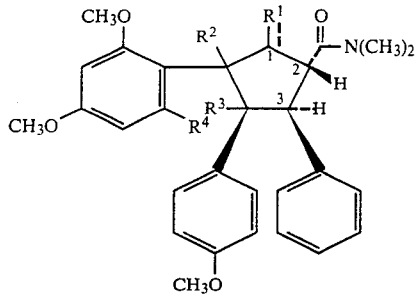

wherein (1)

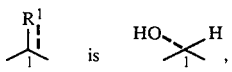

$R^2$ is $\beta$-hydroxy and $R^3$ and $R^4$ together form an oxygen bridge, or (2)

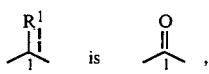

$R^2$ and $R^3$ together form an additional carbon-carbon bond, and $R^4$ is hydroxy, are disclosed. These compounds exhibit antileukemic activity against P388 lymphocytic leukemia in $CDF_1$ mice and inhibitory activity in vitro against cells derived from human epidermoid carcinoma of the nasopharynx(KB) cells.

3 Claims, No Drawings

1H-CYCLOPENTA[B]BENZOFURAN DERIVATIVE AND ITS ANALOG

The present invention relates to a substantially pure 1H-cyclopenta[b]-benzofuran derivative isolated from *Aglaia elliptifolia* Merr. and its analog.

*Aglaia elliptifolia* Merr. is an evergreen small plant indigenous to southern Taiwan, and has been reported to contain dimethylterephthalate, aglaic acid, β-sitosterol, stigmasterol, campesterol and monoglucosides of β-sitosterol and stigmasterol in *Med. Sci.*, 1975, 1, 11. It has also been reported in this literature that the alcoholic extract of dried roots and stems of *Aglaia elliptifolia* Merr. has antileukemic activity and inhibitory activity in vitro against cells derived from human epidermoid carcinoma of the nasopharynx cells. To our best knowledge cyclopentabenzofuran derivatives and triphenyl-substituted pentanone derivatives having antileukemic activity are not known.

The present inventors have found that a novel compound isolated from *Aglaia elliptifolia* Merr. exhibits potent antileukemic activity against P388 lymphocytic leukemia in $CDF_1$ mice and inhibitory activity in vitro against cells derived from human epidermoid carcinoma of the nasopharynx(KB) cells, and accomplished the present invention.

The compounds of the present invention are represented by the general formula:

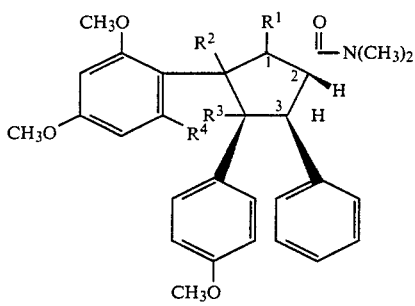

wherein

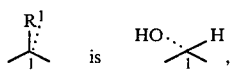

$R^2$ is β-hydroxy and $R^3$ and $R^4$ together form an oxygen bridge, or

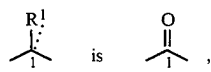

$R^2$ and $R^3$ together form an additional carbon-carbon bond, and $R^4$ is hydroxy.

The compounds of formula (I) include 1α,8bβ-dihydroxy-6,8-dimethoxy-2α-N,N-dimethylcarbamido-3aβ-4'-methoxyphenyl-3β-phenyl-2,3,3a,8b-tetrahydro-1H-cyclopenta[b]benzofuran (hereinafter referred to as "Rocaglamide"), and 2-(2',4'-dimethoxy-6'-hydroxyphenyl)-5α-N,N-dimethylcarbamido-3-(4'-methoxyphenyl)-4β-phenylcyclopenta-2-en-1-one (hereinafter referred to as "Dehydrorocaglamide"). These compounds are represented by the following formulae.

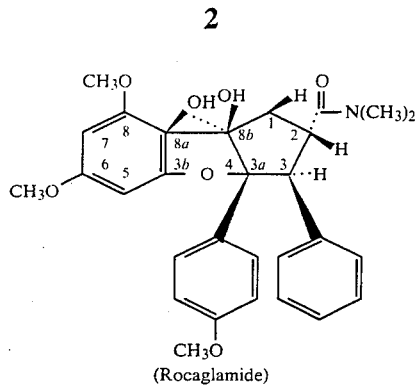
(Rocaglamide)

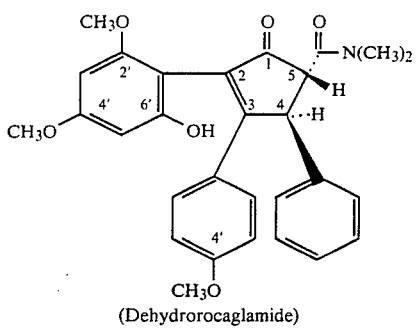
(Dehydrorocaglamide)

The compounds of this invention may be, for example, obtained in their substantially pure form by the following procedures.

(1.a) The fresh stem barks as well as the fresh barks of roots of *Aglaia elliptifolia* Merr. are peeled, dried and powdered. The powder thus obtained is exhaustively extracted first by a lower alcohol such as methanol, ethanol or propanol in a Soxhlet type extractor under vacuum. The alcoholic extract is concentrated under vacuum to yield viscous extract. The alcoholic extract is then defatted by extraction with a lower alkane such as n-pentane, n-hexane or n-heptane, or petroleum ether. Alternatively, the powder may be thoroughly defatted first by extraction with an alkane as mentioned above or with petroleum ether in a Soxhlet type extractor under vacuum and then extracted by the alcohol as mentioned above.

(1.b) The alcoholic viscous extract obtained as in (1.a) above, if it has not been defatted before alcohol extraction, is then dissolved in 7-10 v/w of 50% methanol or 50% ethanol. The insoluble residue is not filtered out at this stage and this solution is exhaustively extracted with about ⅔ volume of petroleum ether or a lower alkane as mentioned above several times by shaking in a separatory funnel or by a suitable device. The defatted aqueous-alcoholic solution is then freed from insoluble substances by filtering through a Buncher funnel or other filtering device under reduced pressure or by centrifugation.

(2) The defatted solution obtained as in (1.b) is then evaporated under vacuum to near dryness and then extracted with ether by shaking or stirring in a tightly enclosed vessel in a cool room to yield ether soluble Rocaglamide-rich fraction I and ether insoluble fraction II. Both fractions I and II are evaporated to dryness separately, and the fraction II is further extracted with chloroform or dichloromethane to yield Rocaglamide-rich fraction III.

(3) The dried Rocaglamide-rich fraction I is fractionated by absorption chromatography by solvent mixtures with increasing polarity of the following order: ether, chloroform, ethyl acetate, acetone and methanol. The fractions containing Rocaglamide are tested by thin layer chromatography (TLC) and evaporated to dryness to yield fraction I-2.

(4) Fraction III is chromatographed on a silica gel column and is eluted by solvent mixtures of increasing polarity in the following sequence: ether, chloroform, ethyl acetate, acetone and methanol. The chromatographic fractions containing Rocaglamide are detected by thin layer chromatography, combined, and evaporated to dryness to yield fraction III-2.

(5) Fractions I-2 and III-2 are combined and subjected to column chromatography (e.g., silica gel low pressure lobar column, chloroform-ethyl acetate) or to preparative HPLC (e.g., Prep PAK-500/Silica HPLC column, chloroform-ethyl acetate). The fractions containing Rocaglamide as detected by TLC are combined. These crude fractions are purified by molecular sieve chromatography using Sephadex LH-20 (Pharmacia Fine Chemicals), and recrystallized from methanol (or other suitable solvents) to yield Rocaglamide in a monoclinic crystalline, substantially pure form.

(6) Rocaglamide is dissolved in an organic solvent such as anhydrous methanol or ether. To the solution is added conc. hydrochloric acid at room temperature. The reaction mixture is evaporated to dryness, subjected to absorption chromatography and eluted with benzene-chloroform-methanol to yield crystals which are recrystallized from an lower alcohol such as methanol or ethanol to give substantially pure Dehydrorocaglamide.

Rocaglamide when recrystallized from methanol exists in monoclinic methanol solvate, and is characterized by mass spectrometry, $^1$H-NMR, $^{13}$C-NMR, UV, OR spectrophotometry and also X-diffractometry. Chemical characterization is done by decomposing Rocaglamide in HCl-Methanol to yield Dehydrorocaglamide and the structure of Dehydrorocaglamide is determined by mass spectrometry, $^1$H-NMR, $^{13}$C-NMR, IR spectrophotometry and also by X-diffractometry.

The compounds of this invention exhibit potent antileukemic activity against P388 lymphocytic leukemia in CDF$_1$ mice and inhibitory activity in vitro against cells derived from human epidermoid carcinoma of the nasopharynx(KB) cells, therefore, they can be used as antileukemic and anti-KB agents in mammals. For these purposes, the compounds of this invention may be administered orally, intravenously or intramuscularly in conventional forms such as tables, capsules, powders, syrups and injectionable forms prepared according to conventional pharmaceutical practices. The dosage level with the compound of this invention depends on the size of the host mammal, nature and size of the tumor and the like. Generally, however, the daily dosage may range from 0.1 to 10 mg/kg of body weight in single or divided doses.

The following tests show that the compounds of this invention exhibit antileukemic activity against P388 lymphocytic leukemia in CDF$_1$ mice and inhibitory activity in vitro against cells derived from human epidermoid carcinoma of nasopharynx cells.

In vivo procedure: Each of the compounds to be tested is dissolved in a minimum amount of 95% ethanol, and the alcoholic solution is dispersed in a 0.5% aqueous solution of Klucel (Hydroxy propylcellulose) and is then ready for testing. Transplantation was carried out using aseptic procedures including the use of sterilized instruments and hooded areas. The sterility of each tumor was tested by inoculation in thioglycollate broth medium. The entire experiment was discarded if bacterial growth occurred within 48 hours of incubation. The DBA/2 mice were used for propagation and CDF$_1$ mice were used for the tests. The transplanatation of leukemia cells was made by intraperitoneal inoculation of Day 0 of 0.1 ml diluted ascitic fluid containing $10^6$ cancer cells. The animals were randomized on Day 1 into test groups of six or four and control groups of $6 \times \sqrt{n}$ or $4 \times \sqrt{n}$ which were tested simultaneously against n samples. The treatment was started on Day 1 and continued through Day 10. All the survivals were sacrificed on Day 30. The ratio of median survival time (in days) of the treated group to that of the control group in percent (T/C $\times$ 100 = X%) was calculated.

Deaths before Day 6 were considered nonleukemic and formed the basis of toxic evaluations. When a toxic result (over two deaths among 6 or 4 animals) was observed, the test was repeated at an appropriately lower dose until the maximum tolerated dose was reached. In addition, if the T/C value for the survival test was <85%, the dose was considered too high and the test was repeated at a lower dose.

In addition to the sterility test and frequent replacement of standardized tumor lines, the quality of the P388 leukemia was also controlled by the establishment of limits for death, "no takes" and means of survival time among control aminals; deaths exceeding 10% among animals in the control group were considered excessive. Experiments in which the control animals which fell outside of these limits were evaluated and some or all tests were repeated as deemed necessary.

A positive control was used in order to detect the range of susceptibility of tumor lines to the tested compound and technical errors which might occur. Cyclophosphamide at a dose of 22.5 mg/kg/day with a limit of T/C$\leqq$135% was used for the positive control. A tested compound with a result of T/C$\leqq$125% at a nontoxic dose is considered to be active.

The antileukemic effects of the compounds of this invention are summarized in Table I.

TABLE I

|  | Dose (mg/kg) | T/C % |
| --- | --- | --- |
| ethanol ext.* | 150 | 145 |
| Rocaglamide | 1 | 156 |
| Dehydrorocaglamide | 20 | 130 |

*the ethanol extract of *Aglaia elliptifolia* Merr. in Example 1 described below.

Cell culture procedure: The bioassay procedure used for the compounds of this invention as described below is that published by Geran et al in *Cancer Chemother. Rep.*, Part 3, 3,1, (1972). Human nasopharynx epidermoid carcinoma (KB) cells maintained on Eagle's basal medium plus 10% of suitable serum and P388 mouse leukemia cells from DBA/2 mice ascitic fluid were used in this bioassay. About 50,000 cells in 1 ml of medium were implanted in a series of replicate 15-mm screw-cap culture tubes and incubated at 37° C. for 24 hours. The medium of each tube was removed and fresh medium containing the test compound was added and again incubated. The cultures were re-fed at 72 hours and the protein content was determined 1 to 2 days thereafter according to the method of Oyama and Eagle (Oyama, V.I. and Eagle, H., "Measurement of Cell Growth in Tissue Culture with a Phenol Reagent", *Proc. Soc. Exp. Biol. Med.*, 91: 305–307, (1956)). A test compound with an $ED_{50} < 14$ μg/ml is considered to be active.

The activities of Rocaglamide against P388 and KB cell cultures, as expressed as $ED_{50}$, were $2.1 \times 10^{-2}$ mcg/ml and $1.0 \times 10^{-3}$ mcg/ml, respectively.

This invention is further illustrated by the following examples:

EXAMPLE I

The stem and root barks of *Aglaia elliptifolia* Merr. were dried and powdered into fine powder, and 8 kg of such powder was thoroughly extracted with 95% ethyl alcohol in a stainless steel Soxhlet type extractor under reduced pressure for 10 days. The alcoholic extracts was separated by centrifugation and the clear solution was evaporated under vacuum to yield a syrupy liquid (900 ml). To this concentrated extract 1000 ml of chloroform was added, and the mixture was extracted by constant shaking in a tightly closed 5000 ml glass bottle in a cool room for 4 hours. The chloroform layer was separated and the partition procedure was repeated three times with fresh charges of chloroform. The chloroform extracts were combined (4000 ml) and evaporated to dryness to yield 530 g of fraction Fr-A₁. Fraction Fr-A₁ was thoroughly extracted 4 times, each time by shaking with 800 ml of ether in a tightly closed 4000 ml glass bottle in a cool room. The ether extracts were combined and evaporated to dryness to yield ether soluble fraction Fr-A₃ (320 g) and ether insoluble fraction Fr-A₂ (95 g). Ether insoluble fraction Fr-A₂ was further extracted thoroughly four times, each time with 200 ml of chloroform by constant shaking in a tightly closed 1000 ml glass bottle in a cool room. The chloroform extracts were combined and evaporated to dryness to yield 80 g of chloroform soluble fraction Fr-A₄. The ether soluble fraction Fr-A₃ (320 g) was dissolved in methanol, 200 g of silica gel powder (E. Merck) was added, and the mixture was evaporated in a vacuum rotary evaporator to dryness. The dried mixture was packed on top of 1300 g of silica gel powder (E. Merck) in a glass chromatography column (8 cm × 60 cm). The column was the eluted thoroughly with chloroform (5000 ml) and then eluted with ethyl acetate (3000 ml). The ethyl acetate eluted solution containing Rocaglamide was tested by thin layer chromatography (E. Merck pre-coated silica gel plate, developed by benzene:chloroform:methanol=4:6:1 solvent mixture, Rf value of Rocaglamide=0.75). This ethyl acetate eluted solution was evaporated to dryness to yield fraction Fr-A₅ (42 g). The chloroform soluble fraction Fr-A₄ (80 g) as obtained above was similarly fractionated by column chromatography on 400 g of silica gel, the column was first thoroughly eluted with chloroform (5000 ml) and then with ethyl acetate (7000 ml), and this ethyl acetate eluted solution was evaporated to dryness to yield 15 g of fraction Fr-A₆. The Rocaglamide rich fractions Fr-A₅ and Fr-A₆ were combined and labelled as fraction Fr-A₇ (57 g). An aliquot portion (14.5 g) of fraction Fr-A₇ was rechromatographed on 120 g of silica gel in a column (4 cm × 45 cm) and was eluted gradiently with a chloroform-ethyl acetate mixture. The chlromatographic fractions were tested by TLC (E. Merck pre-coated silica gel plate, developed by benzene:chloroform:methanol=4:6:1 solvent mixture, Rf value of Rocaglamide=0.75). The fractions containing Rocaglamide were combined and the combined solution was evaporated to dryness to yield fraction Fr-A₈ (2.5 g). The Rocaglamide rich fraction Fr-A₈ was separated by molecular sieve chromatography on 200 g of Sephadex LH-20 (Pharmacia Fine Chemicals, Switzerland, inside diameter of glass column—4 cm). This LH-20 column was eluted with anhydrous methanol and the fractions were tested by TLC (E. Merck silica gel pre-coated plate, developed by benzene:chloroform:methanol=4:6:1 solvent mixture, Rf value of Rocaglamide=0.75). The Rocaglamide rich fractions were combined and the combined solution was evaporated to dryness to yield fraction Fr-A₉ (1.8 g). Rocaglamide in fraction Fr-A₉ was isolated by absorption chromatography on silica gel (E. Merck pre-packed Lobar column size C), the column was eluted by a solvent mixture (benzene:chloroform:methanol=4:6:1) and the eluted fractions were tested by TLC (E. Merck pre-coated silica gel plate, developed by benzene:chloroform:methanol=4:6:1 solvent mixture). The Rocaglamide rich fractions were combined and the combined solution was evaporated to dryness to yield 320 mg of crystalline Rocaglamide and it was recrystallized from anhydrous methanol.

m.p. 118°–119° C.

MS: 505.2087 (M⁺)

$[\alpha]_D^{25} = -96°$ (C, 1.00, CHCl₃)

UV $\lambda_{max}^{C_2H_5OH}$ nm (log ε): 211(log ε 4.38), 232(sh, log ε 3.96), 273(log ε 2.91)

IR $\nu_{max}^{KBr}$ cm⁻¹: 1625, 3430

¹H-NMR(CDCl₃): δ=1.68(bs, OH, disappeared upon the treatment with D₂O), 1.9(bs, OH̄, disappeared upon the treatment with D₂O), 2.94(s, 3H), 3.31(s, 3H), 3.88(dd, 1H, J 6.8 Hz, 14 Hz, H-2), 4.32(dd, 1H, J 14 Hz, H-3), 5.01(1H̄, J 6.8 Hz, H-1)

¹³C-NMR(CDCl₃) was shown as follows:

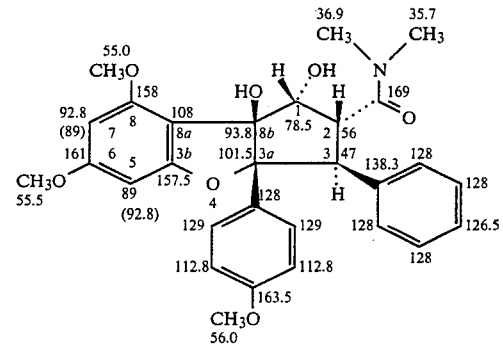

A single-crystal X-ray analysis, monoclinic, space group P 2₁, a=14.260(6), b=7.822(3), C=12.323(5)Å, β=98.01(2)°, U=1361.1Å³, Z=2, D_c=1.273 gcm⁻¹

EXAMPLE 2

The stem and root barks of *Aglaia elliptifolia* Merr. were dried and pulverized into fine powder and 11 kg of such powder were thoroughly extracted with 95% ethyl alcohol in a stainless Soxhlet type extractor under reduced pressure for 10 days. The alcoholic extract was separated by centrifugation and the clear extract was concentrated under vacuum to yield 1200 g of a syrupy extract. This alcoholic extract was extracted by constant shaking in a tightly closed 5000 ml glass flask in a cool room with 1000 ml of chloroform for 4 hours. The extraction process was repeated with fresh portions of 800 ml each of chloroform an additional three times.

The chloroform extracts were combined and evaporated to dryness to yield a chloroform soluble fraction Fr-B$_1$ (950 g). This chloroform soluble fraction Fr-B$_1$ was extracted to eliminate fatty substances by shaking for 4 hours in a tightly closed 5000 ml glass bottle in a cool room with 1000 ml of petroleum ether, and the extraction process was repeated an addition 3 times, each time using 1000 ml of petroleum ether. The petroleum ether insoluble fraction Fr-B$_2$ (800 g) resulting from this extraction process was separated by absorption chromatography on 5000 g of silica gel (E. Merck, inside diameter of glass column=9.5 cm). The column was eluted in successive sequence by 5000 ml of each of the following solvents: n-hexane: ether (1:2), ether, ethyl acetate, and finally by ethanol. The eluted fractions were tested by TLC (E. Merck pre-coated silica gel plate, developed by benzene:chloroform:methanol=4:6:1 solvent mixture, Rf value of Rocaglamide=0.75). The ethyl eluted fractions containing Rocaglamide were combined and evaporated to dryness to yield 87 g of fraction Fr-B$_3$. Fraction Fr-B$_3$ was extracted thoroughly by shaking in a tightly closed 1000 ml glass bottle in a cool room with 250 ml of ether, and the extraction process was repeated an additional three times, each time with 150 ml of fresh ether. The ether extracts were combined and evaporated to dryness to yield 42 g of ether soluble fraction Fr-B$_4$. The ether soluble fraction Fr-B$_4$ (42 g) was separated by absorption chromatography on 400 g of silica gel (E. Merck, inside diameter of glass column—3 cm). The column was eluted with a solvent mixture (benzene:chloroform:methanol=8:6:1). The eluted fractions were tested by TLC (E. Merck pre-coated silica gel plate, developed by benzene:chloroform:methanol=4:6:1 solvent mixture, Rf value of Rocaglamide=0.75). The chromatography fractions containing Rocaglamide were combined and evaporated under vacuum to dryness to yield 24 g of the Rocaglamide rich fraction Fr-B$_5$. Al aliquot portion of 4 g of fraction Fr-B$_5$ was further chromatographed on 200 g of Sephadex LH-20 (Pharnacia Fine Chemicals, Switzerland, inside diameter of glass column=4 cm). The LH-20 column was eluted by methanol. The LH-20 column fraction was tested by TLC (E. Merck pre-coated silica gel plate, developed by benzene:chloroform:methanol=4:6:1 solvent mixture, Rf value of Rocaglamide=0.75). The fractions containing Rocaglamide were combined and the solvent evaporated to dryness to yield 1.5 g of fraction Fr-B$_6$. Rocaglamide of fraction Fr-B$_6$ was isolated by low pressure absorption chromatography on silica gel by using pre-packed Lobar column (E. Merck, size B). The column was eluted by a solvent mixture (benzene:chloroform:methanol=4:6:1) to yield 800 mg of crystalline Rocaglamide which was then recrystallized from anhydrous methanol.

EXAMPLE 3

The bark of the roots and stems of the plant *Aglaia elliptifolia* Merr. were dried and pulverized to a fine powder. Twelve kg of this powder was extracted exhaustively in a stainless steel Soxhlet type extractor with 95% ethyl alcohol under reduced pressure for 10 days. The alcoholic extract was separated by centrifugation and the clear supernatant was evaporated to a syrupy liquid (850 g). The viscous alcoholic extract was extracted thoroughly in a tightly closed 5000 ml glass bottle by constant shaking in a cool room with 1000 ml of petroleum ether for 4 hours. The extract was separated by centrifugation and the clear supernatant was evaporated to yield a syrupy liquid (850 g). The viscous alcoholic extract was extracted thoroughly in a tightly closed 5000 ml glass bottle by constant shaking in a cool room with 1000 ml of petroleum ether for 4 hours. The extraction was repeated an additional 3 times to yield 604 g of a petroleum ether soluble fraction Fr-C$_1$ and 180 g of a petroleum ether insoluble fraction. The petroleum ether insoluble fraction was extracted by constant shaking for 4 hours with 300 ml of ether in a well closed 1000 ml glass bottle in a cool room. The ether extraction process was repeated an additional 3 times and separated into an ether soluble fraction Fr-C$_2$ (125 g) and an ether insoluble fraction (55 g) which was further extracted with 100 ml of chloroform in a tightly closed 500 ml glass bottle by constant shaking in a cool room, and the process was repeated an additional 3 times to yield 43 g of a chloroform soluble fraction Fr-C$_3$ and a chloroform insoluble fraction Fr-C$_4$ (11 g). Fractions Fr-C$_3$ and Fr-C$_2$, both containing Rocaglamide as tested by TLC (E. Merck pre-coated plate, developed by benzene:chloroform:methanol=4:6:1, Rf value of Rocaglamide=0.75), were combined and chromatographed on 2000 g of silica gel (E. Merck, inside diameter of glass column=7 cm), and the column was eluted successively with 5000 ml each of chloroform, ethyl acetate and lastly with methanol. The chromatography fractions were tested by TLC as above and the fractions containing Rocaglamide were combined and evaporated to dryness to yield 67 g of fraction Fr-C$_5$. An aliquot portion of 3 g of fraction Fr-C$_5$ was chromatographed by pre-packed silica gel Lobar Column (E. Merck, size B) by low pressure chromatography using benzene:chloroform;methanol=4:6:1 as eluent. The eluted fractions were tested by TLC in the same manner as mentioned above, and the Rocaglamide fractions were combined and evaporated to dryness to yield 150 mg of Rocaglamide, which was then recrystallized from anhydrous methanol to yield a monoclinic crystalline product.

EXAMPLE 4

The stem and root barks of *Aglaia elliptifolia* Merr. were dried and powdered into a fine powder and 11 kg of such powder were thoroughly extracted with 95% ethyl alcohol in a stainless Soxhlet type extractor under reduced pressure for 10 days. The alcoholic extract was separated by centrifugation and the clear supernatant was concentrated under vacuum to yield a syrupy viscous extract which weighed 800 g. This alcoholic extract was extracted by shaking in a tightly closed 5000 ml glass bottle with 1000 ml of ether in a cool room 7–10 times. The ether extracts were combined and evaporated to dryness to yield 450 g of a Rocaglamide rich fraction Fr-D$_1$. Fraction Fr-D$_1$ was extracted thoroughly by shaking with 800 ml of n-hexane in a tightly closed 2000 ml glass bottle in a cool room for 4 hours. The n-hexane extract was filtered and the insoluble substance was further extracted with fresh n-hexane in the same manner 3 times. The n-hexane insoluble Rocaglamide rich fraction Fr-D$_2$ weighing 65 g was chromatographed on 1.4 kg of silica gel (E. Merck, 70–230 mesh) column (8 cm×60 cm), and was eluted successively with ether (15000 ml), chloroform (4000 ml) and ethyl acetate (30000 ml). The eluted fractions were tested by TLC (silica gel plate, E. Merck, developing solvent: benzene:chloroform:methanol=4:6:1). Since the anti-KB activity resides in the ethyl acetate eluted fractions the active fractions were combined and evaporated to dryness to yield fraction Fr-D₃ (18 g). Fraction Fr-D₃ was further chromatographically seperated using a molecular sieve Sephadex LH-20 column (800 g) (Pharmacia Fine Chemicals, Switzerland). The column was eluted by anhydrous methanol, and the eluted fractions (50 ml for each fraction) were tested by TLC (silica gel pre-coated plate, E. Merck, developing solvent mixture: benzene:chloroform:methanol=4:6:1, Rf value of Rocaglamide=0.75). The fractions containing Rocaglamide were combined and evaporated to dryness to yield fraction Fr-D₄ (6.9 g). Fraction Fr-D₄ was further fractionated chromatographically by medium low pressure absorption chromatography (silica gel pre-packed Lobar column, size B, E. Merck). The column was eluted first with benzene (1500 ml), then with benzene:chloroform mixture (1:1, 1500 ml) and then with benzene:chloroform:methanol mixture (4:6:1, 4000 ml). The chromatography eluted fractions were tested by TLC (E. Merck pre-coated silica gel plate, developed by benzene:chloroform:methanol=4:6:1 solvent mixture), and the fractions containing Rocaglamide (Rf—0.75) were combined and evaporated to yield 600 mg of crystalline Rocaglamide. This crystalline Rocaglamide was further purified by recrystallization from anhydrous methanol.

EXAMPLE 5

Five hundred mg of Rocaglamide were dissolved in 5 ml of anhydrous methanol in a 15 ml glass stoppered flask and 4 drops of concentrated hydrochloric acid were added. The mixture was left at room temperature with occasional shaking overnight. The reaction mixture was evaporated under vacuum to dryness at a low temperature of not over 30° C. and the last traces of hydrochloride were eliminated by keeping the residue in a vacuum desiccator over solid sodium hydroxide for 24 hours. The reaction mixture was then separated by absorption column chromatography on 15 g silica gel (E. Merck), using a glass column with inside diameter—1 cm. The column was eluted with a benzene:chloroform:methanol (8:8:1) mixture to yield 60 mg of colorless crystalline Dehydrorocaglamide, which was then recrystallized from methanol.

m.p. 233°–234° C.
MS: 487.1980 (M+)
$[\alpha]_D^{25} = +435°$(C, 0.2, CHCl₃)
UV $\lambda_{max}^{C_2H_5OH}$ nm (log ε): 312(log ε 3.71)
IR $\nu_{max}^{KBr}$ cm⁻¹: 1700
¹H-NMR(CDCl₃): δ=3.69, 3.70, 3.80(s, 3H, —OCH₃); 2.9, 3.04(s, 3H, —NCH₃)

A single-crystal X-ray analysis showed an orthorhombic, space group P 2₁ 2₁ 2₁, a=14.103(6), b=19.871(8), c=9.166(4)Å, U=2568.7Å³, Z-4, D_c=1.261 gcm⁻³.

We claim:
1. A substantially pure compound of the formula

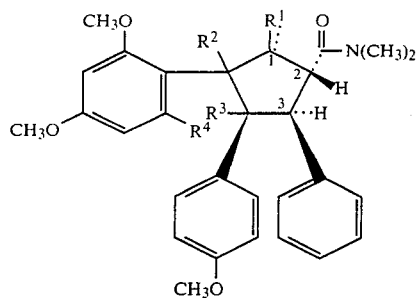

wherein

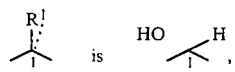

R² is β-hydroxy and R³ and R⁴ together form an oxygen bridge, or

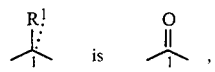

R² and R³ together form an additional carbon-carbon bond, and R⁴ is hydroxy.

2. A substantially pure compound of the formula

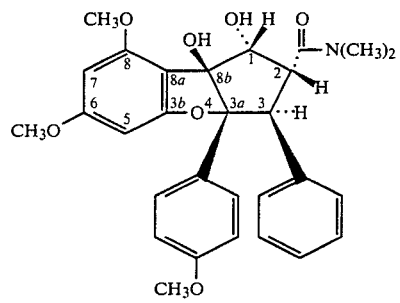

3. A substantially pure compound of the formula

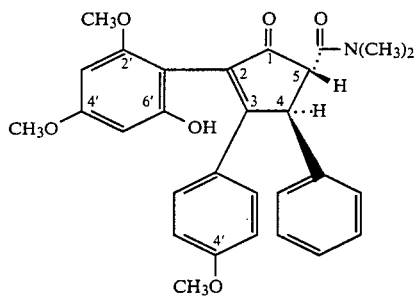

* * * * *

UNITED STATES PATENT AND TRADEMARK OFFICE
CERTIFICATE OF CORRECTION

PATENT NO. : 4,539,414

DATED : September 3, 1985

INVENTOR(S) : KING et al

It is certified that error appears in the above-identified patent and that said Letters Patent is hereby corrected as shown below:

Col. 2, the formula at the top of Col. 2 should appear as follows:

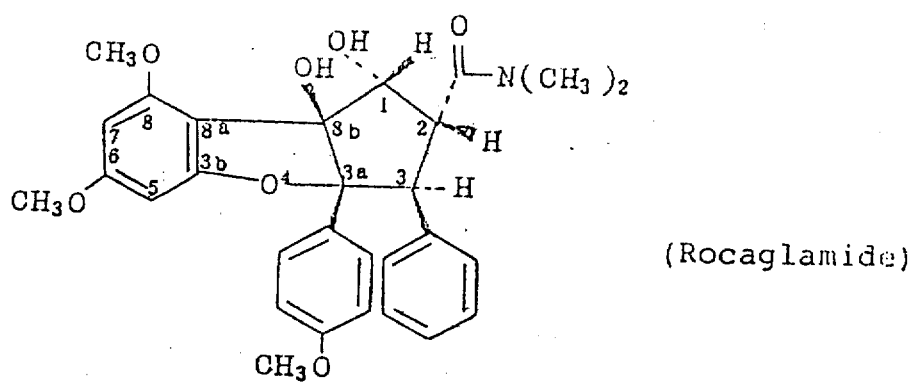

(Rocaglamide)

Col. 2, line 57, "Buncher" should read --Buchner--.

Col. 3, line 38, "OR" should read --IR--; and
line 43, after "NMR" insert --UV,--.

Col. 4, line 41, "$\leq$" should read --$\geq$--; and
line 42, "$\leq$" should read --$\geq$--.

Col. 5, line 64, "chlromatographic" should read --chromatographic--.

UNITED STATES PATENT AND TRADEMARK OFFICE
CERTIFICATE OF CORRECTION

PATENT NO. : 4,539,414

DATED : September 3, 1985

INVENTOR(S) : KING et al

It is certified that error appears in the above-identified patent and that said Letters Patent is hereby corrected as shown below:

Col. 7, line 38, "Al" should read —An—; and
line 40, "Pharnacia" should read —Pharmacia—.

Col. 9, line 3, "seperated" should read —separated—.

Claim 1, the formula should appear as follows:

1. A substantially pure compound of the formula

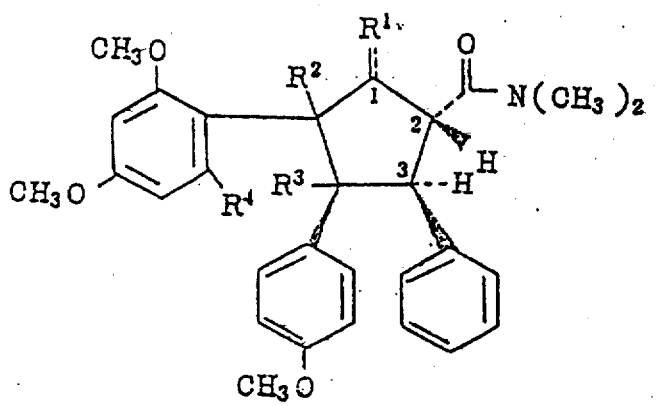

UNITED STATES PATENT AND TRADEMARK OFFICE
CERTIFICATE OF CORRECTION

PATENT NO. : 4,539,414

DATED : September 3, 1985

INVENTOR(S) : KING et al

It is certified that error appears in the above-identified patent and that said Letters Patent is hereby corrected as shown below:

wherein 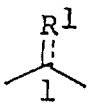 is 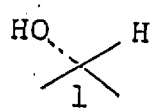 , $R^2$ is β-hydroxy and $R^3$ and $R^4$ together form an oxygen bridge, or 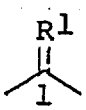 is 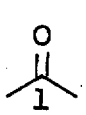 , $R^2$ and $R^3$ together form an additional carbon-carbon bond, and $R^4$ is hydroxy.

Signed and Sealed this

Twenty-fourth Day of June 1986

[SEAL]

Attest:

DONALD J. QUIGG

Attesting Officer     Commissioner of Patents and Trademarks